United States Patent [19]

Beevor et al.

[11] Patent Number: 5,442,107
[45] Date of Patent: Aug. 15, 1995

[54] PREPARING CARBOXYLIC ACIDS

[75] Inventors: Robert G. Beevor; David J. Gulliver, both of North Humberside, England

[73] Assignee: BP Chemicals Limited, London, England

[21] Appl. No.: 127,890

[22] Filed: Sep. 28, 1993

Related U.S. Application Data

[63] Continuation of Ser. No. 866,102, Apr. 7, 1992, abandoned, which is a continuation of Ser. No. 603,664, Oct. 26, 1990, abandoned.

[30] Foreign Application Priority Data

Apr. 6, 1989 [GB] United Kingdom ................ 8907763
Aug. 15, 1989 [GB] United Kingdom ................ 8918588

[51] Int. Cl.⁶ ............................................. C07C 51/12
[52] U.S. Cl. ..................................... 562/519; 554/154
[58] Field of Search ......................... 562/519; 554/154

[56] References Cited

U.S. PATENT DOCUMENTS

| 4,430,273 | 2/1984 | Erpenbach | 562/891 |
| 4,853,482 | 8/1989 | Drury et al. | 562/607 |

FOREIGN PATENT DOCUMENTS

| 1111065 | 10/1981 | Canada . |
| 055618 | 7/1982 | European Pat. Off. . |
| 0079461 | 5/1983 | European Pat. Off. . |
| 087870 | 7/1983 | European Pat. Off. . |
| 87869 | 9/1983 | European Pat. Off. ............ 562/517 |
| 0109212 | 5/1984 | European Pat. Off. . |
| 0153834 | 9/1985 | European Pat. Off. . |
| 0161874 | 11/1985 | European Pat. Off. . |
| 1233121 | 5/1971 | United Kingdom . |
| 1538783 | 1/1979 | United Kingdom . |
| 2106511 | 4/1983 | United Kingdom . |

OTHER PUBLICATIONS

Applied Industrial Catalysis, vol. 1, pp. 275-296 (1983).

Primary Examiner—José G. Dees
Assistant Examiner—Joseph M. Conrad, III
Attorney, Agent, or Firm—Brooks Haidt Haffner & Delahunty

[57] ABSTRACT

A process for preparing a carboxylic acid having (n+1) carbon atoms (e.g. acetic acid) from an alcohol having n carbon atoms (e.g. methanol) by liquid phase, rhodium catalyses carbonylation is provided. The process is characterized by using a catalyst stabilizer selected from certain classes of imidazolium iodides, alkyl substituted pyridinium iodides and hydroxypyridinium iodides. Most preferred are those derived from the amines 2-ethyl-4-methyl imidazole, 4-ethylpyridine, 4-t-butylpyridine and 3,4-lutidine by quarternisation with a methyl group.

8 Claims, No Drawings

PREPARING CARBOXYLIC ACIDS

This application is a continuation of application Ser. No. 07/866,102, filed Apr. 7, 1992, now abandoned, which is a continuation of application Ser. No. 07/603,664, filed Oct. 26, 1990, now abandoned.

The present invention relates to an improved process for making carboxylic acids having (n+1) carbon atoms by the carbonylation of alcohols having n carbon atoms in the presence of rhodium catalysts. In particular the present invention relates to the production of acetic acid by the carbonylation of methanol using a rhodium catalyst.

The production of acetic acid by the rhodium catalysed carbonylation of methanol is a well known process which is operated upon a commercial scale. Such a process is an example of a genus of similar processes in which an alcohol having n carbon atoms is converted into a carboxylic acid having (n+1) carbon atoms by carbonylation (i.e. reaction with carbon monoxide). Reaction of the alcohol with carbon monoxide is typically carried out in the liquid phase in the presence of a dissolved rhodium catalyst and a promoter comprising the iodide derivative of the alcohol. The process is further described generically in GB 1233121 whilst Applied Industrial Catalysis volume 1 p 275–296 (1983) details the conversion of methanol to acetic acid.

As a result of much basic research, it is now believed that the rhodium species responsible for catalysis in such processes is the rhodium (I) anion $[Rh(CO)_2I_2]^-$. Mechanistic studies suggest that catalysis is effected by a cycle of reaction steps involving inter alia the generation of a rhodium (III) species by oxidative addition of the iodide derivative of the alcohol to $[Rh(CO)_2I_2]^-$ and the subsequent regeneration of $[Rh(CO)_2I_2]^-$ by reductive elimination of an acyl iodide from the rhodium (III) species. This cycle of oxidation and reduction reactions between the rhodium (I) and rhodium (III) oxidation states leads to a problem because, under certain conditions, rhodium (III) species eg $RhI_3$ or $Rh(CO)I_5^{2-}$ salts are generated which are either sparingly soluble or insoluble in the medium in which the process is carried out. Hence there is a tendency for catalyst precipitation to occur and for all practical purposes irreversible removal of rhodium from the catalyst cycle. Such loss of catalyst from the reaction medium and catalyst cycle is unacceptable firstly because it causes the productivity of the process to decrease and secondly because the rhodium, which is extremely valuable, is difficult to recover.

It has been observed that precipitation of insoluble rhodium (III) species has the greatest tendency to occur when the levels of carbon monoxide are low and/or when the process is operated in the presence of less than 14–15% by weight water. On a commercial scale, the former tendency can cause problems in those parts of a methanol carbonylation plant where the overpressure of carbon monoxide is low, whilst the latter has meant that most methanol carbonylation plants have typically operated with a standing concentration of about 14–15% by weight water in the carbonylation reactor.

An approach to solving the problem of rhodium (III) species precipitation has been described in EP 55618 and EP 161874. EP 55618 discloses that the tendency of rhodium catalysts to precipitate in those parts of an alcohol carbonylation plant which are carbon monoxide deficient (eg flash tanks, transfer pipes and recycle loops) can be overcome by having a catalyst stabiliser present in the plant. Preferred stabilisers are (a) $N,N,N^1,N^1$-tetramethyl-o-phenylenediamine and 2,3'dipyridyls, (b) substituted diphosphines of formula $(R_1)(R_2)P-R_3-P(R_4)(R_5)$, (c) dibasic or polybasic carboxylic acids having the formula $HOOC-Y_1-COOH$ and $(HOOC-Y_2)(HOOC-Y_3)NY_1N(Y_4COOH)(Y_5-COOH)$ and (d) compounds of germanium, antimony, tin or an alkali metal.

A related application EP 1538341 teaches that imidazole or thiol stabilisers can also be used. This application illustrates the use of N-methylimidazole.

EP 161874 teaches that, if a catalyst stabiliser selected from metal iodides and quaternary ammonium iodides is employed, then the tendency of the catalyst to precipitate under low water conditions is reduced. Preferred stabilisers are alkali and alkaline earth metal iodides, eg lithium iodide. The quaternary ammonium iodide N-methylpicolinium iodide is also specifically disclosed.

The prior art discussed above thus shows that, by using one of a number of catalyst stabilisers, it is possible to reduce the tendency of rhodium catalysts to precipitate as an insoluble rhodium (III) species. Recently, however, it has been found that a problem arises when quaternary ammonium iodides, such as N-methylimidazolium. iodide and N-methyl picolinium iodide, are used in that such iodides themselves tend to generate sparingly soluble rhodium containing complexes thereby leading to loss of rhodium.

According to the present invention there is provided a process for preparing a carboxylic acid having (n+1) carbon atoms by reaction of carbon monoxide with an alcohol having n carbon atoms in the presence of a rhodium catalyst which process comprises feeding the alcohol and/or an ester of the alcohol and the carboxylic acid together with carbon monoxide to a carbonylation reactor and removing the carboxylic acid from the carbonylation reactor characterised by maintaining in the carbonylation reactor during the course of the process a liquid reaction medium comprising: (a) at least a finite quantity of water, (b) a catalyst stabiliser selected from the group consisting of quaternary ammonium iodides having the formula:

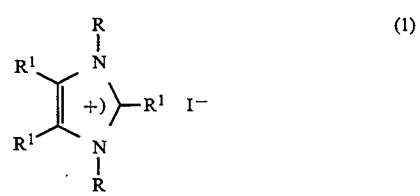

(1)

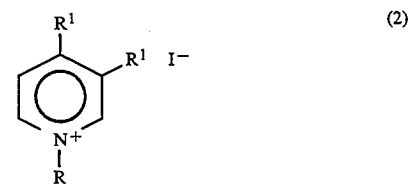

(2)

and

-continued

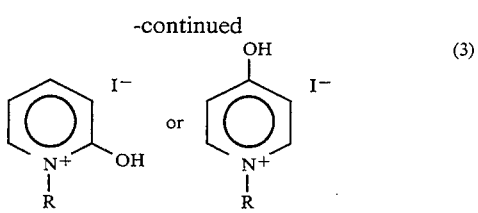
(3)

wherein the R and $R^1$ groups are independently selected from hydrogen or $C_1$ to $C_{20}$ alkyl groups with the proviso that at least one $R^1$ group is other than hydrogen, (d) the iodide derivative corresponding to the alcohol, (e) the ester of the carboxylic acid and the alcohol, (f) a rhodium catalyst, and (g) the carboxylic acid.

The present invention solves the problem defined above by using certain selected quaternary ammonium iodides which have been shown not to generate sparingly soluble rhodium containing complexes even under very severe conditions designed to enhance rhodium precipitation. The quaternary ammonium iodides selected also have the additional advantage that they are particularly effective in preventing precipitation when the water content of the carbonylation reactor is low relative to conventional processes. Indeed they are superior to the stabilisers disclosed in EP 161874.

In a preferred embodiment of the process defined above, the rhodium catalyst and catalyst stabiliser are removed from the carbonylation reactor with the carboxylic acid. The carboxylic acid, rhodium catalyst and catalyst stabiliser are then passed to a zone which is deficient in carbon monoxide relative to the carbonylation reactor and where for example separation of the carboxylic acid from the other components takes place. Thereafter the rhodium catalyst and catalyst stabiliser are recycled to the carbonylation reactor. In the preferred embodiment such a separation and recycle process is characterised by the fact that the rhodium catalyst and catalyst stabiliser are always together when there is a deficiency of carbon monoxide.

Whilst the primary invention and the embodiment can be used when the finite quantity of water in the carbonylation reactor is typical of that used on conventional methanol carbonylation plant (14-15% weight), the technology is especially suitable where the water content of the carbonylation reactor is lower than conventionally used, eg in the range 0.1 to 12% weight preferably 0.5 to 8% weight.

Considering the alcohol having n carbon atoms, whilst this can be in principle be any alcohol having from 1 to 20 carbon atoms and at least one hydroxyl group, the preferred feedstocks are monofunctional aliphatic alcohols having from 1 to 8 carbon atoms. Most preferred feedstocks are methanol, ethanol and propanol with methanol being of prime importance as the methanol to acetic acid process is commericially proven technology.

The overall stoichiometry of the process can be represented by the equation.

$$R^2OH + CO \rightarrow R^2COOH$$

wherein $R^2$ is an organic moiety meeting the criterion defined in the previous paragraph. From this equation the product carboxylic acid obtained for a given alcohol can be readily determined. Thus in the cases of methanol ($R^2 = CH_3$) and ethanol ($R^2 = C_2H_5$), the product carboxylic acids are respectively acetic and propionic acids.

Whilst the processes of the present invention can be operated batchwise, in most cases continuous operation is preferred. During continuous operation the alcohol and/or an ester of the alcohol and the product carboxylic acid are fed to a carbonylation reactor together with the carbon monoxide, sufficient water to maintain a finite concentration in the reactor rhodium catalyst, iodide derivative and catalyst stabiliser. It will be appreciated that, as the last four components are not consumed during the process, they will be continuously recycled to the reactor from the product stream with only the occasional top-up of material as necessary. Corresponding to the continuous feeding of components to the carbonylation reactor, a product stream, comprising product carboxylic acid, water, rhodium catalyst, iodide derivative and catalyst stabiliser, is continuously removed. The net effect of this is that the carbonylation reactor reaches steady state and maintains a liquid reaction medium having steady state composition comprising constant amounts of water, catalyst stabiliser, iodide derivative, ester of the carboxylic acid and the alcohol, rhodium catalyst and carboxylic acid. In practice the carbonylation reactor contains little free alcohol on account of the rapid esterification reaction between the carboxylic acid and the alcohol.

For the processes of the present invention it is preferred that at steady state the liquid reaction medium has a composition in which the individual components fall within the following ranges:

|  | Broad | Preferred |
| --- | --- | --- |
|  | wt % | wt % |
| Water | 0.1-12 | 0.5-8 |
| Ester of Carboxylic Acid and Alcohol | 0.1-10 | 2-8 |
| Iodide derivative | 5-20 | 10-16 |
| Catalyst Stabiliser | 2-20 | 10-20 |
| Rhodium Catalyst (ppm) | 100-1800 | 300-1200 |

Specifically for the carbonylation of methanol to acetic acid the preferred range of compositions is water (0.5%-8%), methyl acetate (2-8%), methyl iodide (10-16%), catalyst stabiliser (10-20%) and rhodium catalyst (300-1200 ppm) with the balance being acetic acid and trace impurities.

The carbonylation reactor is suitably maintained at a temperature in the range 100°-200° C. and at a carbon monoxide pressure in the range 10-200 atmospheres. Preferably the temperature is in the range 140° to 200° C. and the pressure in the range 10-100 atmospheres. Under such conditions the carbonylation reaction occurs rapidly.

Considering the three classes of catalyst stabilisers defined above it is preferred that at least one of the R groups is the same as the $R^2$ group comprising the organic moiety of the alcohol, iodide derivative and carboxylic acid. The $R^1$ groups on the other hand are suitably hydrogen or $C_1$ to $C_8$ alkyl, preferably hydrogen or $C_1$ to $C_6$ alkyl with the proviso defined above. Examples of preferred catalyst stabilisers in each of classes (1) and (2) are those where the $R^1$ groups are selected from hydrogen, methyl, ethyl, n-propyl, iso-propyl, n-butyl, sec-butyl and t-butyl.

One particularly preferred class of catalyst stabilisers are iodide salts of the cation:

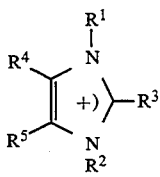

Where
(i) $R^1$ and $R^2$ are methyl
(ii) $R^5$ is hydrogen
(iii) $R^3$ is $C_1$ to $C_{20}$ alkyl or hydrogen and
(iv) $R^4$ is $C_1$ to $C_{20}$ alkyl.

Most preferred examples of this class are where (1) $R^3=C_2H_5$, $R^1,R^2$ and $R^4=CH_3$ and $R^5=H$ or (2) $R^3$ and $R^5=H$, and $R^1,R^2$ and $R^4=CH_3$.

Another particularly important class of catalyst stabiliser is comprised of iodide salts of the cation

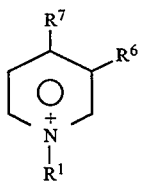

where $R^6$ is either hydrogen or methyl, $R^7$ is $C_1$ to $C_4$ alkyl and $R^1$ is methyl. Preferred examples are where (1) $R^6=H$ and $R^7=C_2H_5$, (2) $R^6=H$ and $R^7=t-C_4H_{g9}$, and (3) and (3) $R^6$ and $R^7=CH_3$.

The catalyst stabilisers can be prepared by quaternising the corresponding amines having the formulae:

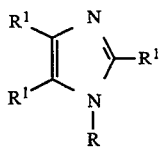 (I)

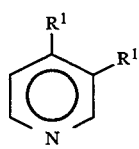 (II)

or

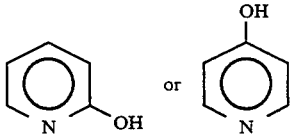 (III)

with an organic iodide of formula RI. The R group in the organic iodide can be the same as or different to any R group in the corresponding amine. It is of course preferred to quaternise those amines corresponding to the preferred catalyst stablisers defined above. In the case where the R groups are $R^2$ it is therefore possible to, generate the catalyst stabiliser in situ by feeding the corresponding amine when the process is started-up or feed or recycle streams are topped-up. Experience has shown that under the operating conditions of the process quaternisation of such amines takes place rapidly.

Once quaternised the catalyst stabiliser will be recycled in the usual way.

The present invention is now illustrated by the following examples:

Experimental Procedure

A. Preparation of the Catalyst Stabiliser 25 mmol of the relevant amine was dissolved in acetic acid along with 25 mmol of methyl iodide. The mixture was heated to 180° C. under nitrogen for 12 hours in a pressure vessel.

B. Test Procedure—Solubility of Quaternary Ammonium Iodide Salts of Rhodium Catalyst The cooled mixture was mixed with further methyl iodide and a stock solution of rhodium in aqueous acetic acid to produce a test solution having the composition:

| | |
|---|---|
| Rhodium | 550 ppm |
| Water | 2% by weight |
| Methyl Iodide | 2% by weight |
| Acetic Acid | balance |

The above test solution was stirred at 25° C. for 1 hour and the resulting liquid analysed for water, ionic iodide and soluble rhodium. The results are shown in the following table:

| ADDITIVE | Water (% w/w) | Final Iodide (% w/w) | Rh (ppm) | % Rh ppt |
|---|---|---|---|---|
| N-methylimidazole | 2.19 | 13.93 | 190.6 | 57.3 |
| 3-picoline | 2.06 | 12.47 | 18.5 | 96.4 |
| Imidazole | 2.36 | 18.92 | 149.4 | 66.5 |
| 2-Ethylimidazole | 2.49 | 19.39 | 79.1 | 82.3 |
| 2-Ethyl-4-methylimidazole | 2.19 | 13.37 | 515.4 | 5.0 |
| Benzimidazole | 2.81 | 13.57 | 59.8 | 89.7 |
| 1,2-Dimethylimidazole | 2.44 | 11.13 | 79.0 | 85.6 |
| 4-Methylimidazole | 2.07 | 12.84 | 519.8 | 5.1 |
| Pyridine | 1.98 | 13.23 | 38.4 | 92.9 |
| 2,6-Lutidine | 2.19 | 14.14 | 41.8 | 92.3 |
| 3,5-Lutidine | 2.23 | 10.39 | 260.7 | 52.1 |
| 3,4-Lutidine | 2.27 | 11.98 | 569.8 | <0.1 |
| 4-t-Butylpyridine | 1.96 | 10.56 | 527.4 | <0.1 |
| 2-Hydroxypyridine | 1.92 | 7.87 | 494.9 | 9.4 |
| 3-Hydroxypyridine | 2.00 | 13.05 | 395.7 | 27.3 |
| 4-Hydroxypyridine | 2.49 | 10.50 | 500.3 | 8.1 |

The results show that for the quaternised ($R=CH_3$) forms of 4-methylimidazole, 2-ethyl-4-methylimidazole (class (1) $R^1=CH_3$ and $C_2H_5$), 3,4-Lutidine (class (2) $R^1=CH_3$), 4-t-butylpyridine, 2-hydroxypyridine and 4-hydroxypyridine, little precipitation of rhodium (III) occurs relative to previously described materials (eg N-methylimidazole, 3-picoline or imidazole).

C. Comparison of Quaternary Ammonium Iodide Stabilisers with Lithium Iodide

The following experiments demonstrate that the quaternary ammonium iodide stabilisers of the present invention are not only more soluble than those previously disclosed (eg imidazole) but also that they are superior to alkali metal iodides in their ability to prevent rhodium precipitation at elevated temperature.

(i) Preparation of Catalyst Stock Solution

Rhodium triiodide (1.57 g), water (7.4 g), hydroiodic acid (0.92 g), and acetic acid (34.0 g) were placed in a Fischer Porter vessel. This was purged and charged with 8 barg carbon monoxide then sealed and heated to 130° C. for 4 hours during which time the RhI$_3$ dissolved to give a clear orange solution.

(ii) Test Procedure—Stabilisation of Rhodium Catalyst by Iodides

In Example 1, catalyst stock solution (2.0 g) and methyl iodide (0.50 g) were added to a solution of LiI (25 mmol) in acetic acid (19.15 g) and stirred for 5 minutes. After sampling the mixture was sealed in a Fischer Porter vessel under 1 bara nitrogen and heated to 180° C. for 22 hours. After cooling this was sampled, both samples being centrifuged then analysed for [Rh], [H$_2$O], and [I$^-$]. For Examples 2 to 4, the amines were quaternised as described for the solubility experiments then treated with catalyst stock solution and methyl iodide as in Example 1.

The results are shown in the following table:

| Example | Additive | Water[1] (% w/w) | Iodide[2] (% w/w) | Init Rh (ppm) | Final Rh (ppm) | % Rh ppt |
|---|---|---|---|---|---|---|
| 1 | LiI | 2.20 | 10.25 | 517.2 | 183.8 | 64.5 |
| 2 | 3,4-Lutidine | 2.09 | 11.92 | 500.6 | 281.3 | 43.8 |
| 3 | 4-t-Butylpyridine | 1.96 | 10.08 | 521.3 | 243.9 | 53.2 |
| 4 | 4-Methylimidazole | 1.76 | 11.43 | 522.3 | 243.5 | 53.4 |

[1] Mean of initial and final water concentrations
[2] Final iodide concentration The reduced catalyst precipitation recorded with the selected quaternary ammonium iodides shows these to be the more effective stabilisers for the rhodium catalyst under the test conditions.

We claim:

1. A process for preparing a carboxylic acid having (n+1) carbon atoms by reaction of carbon monoxide with an alcohol having n carbon atoms wherein n is from 1 to 8 carbon atoms in the presence of a rhodium catalyst which process comprises feeding an alcohol and/or an ester of the alcohol and the carboxylic acid, together with carbon monoxide, to a carbonylation reactor in which there is maintained during the course of the process a liquid reaction medium comprising: (a) at least a quantity of water of about 0.1 to 15% by weight; (b) a catalyst stabilizer which is a quaternary ammonium iodide of a heterocyclic nitrogen compound selected from the group consisting of 2-ethyl-4-methylimidazole, 4-methylimidazole, 4-tert.-butylpyridine, 2-hydroxypyridine, 3-hydroxypyridine and 4-hydroxypyridine; (c) the iodide derivative corresponding to the alcohol, (d) the ester of the carboxylic acid and the alcohol; (e) a rhodium catalyst, and (f) the carboxylic acid, and passing the rhodium catalyst and catalyst stabilizer to a zone which is deficient in carbon monoxide relative to the carbonylation reactor and in which zone separation of carboxylic acid from the other components takes place.

2. A process as claimed in claim 1 characterised in that from 0.5 to 8% weight water is maintained in the carbonylation reactor.

3. A process as claimed in claim 1 characterized in that the catalyst stabilizer is generated in situ in the carbonylation reactor by quaternising a said heterocyclic nitrogen compound with the iodide derivative corresponding to the alcohol.

4. A process as defined in claim 1, wherein the heterocyclic nitrogen compound is 4-t-butylpyridine.

5. A process as defined in claim 1, wherein the heterocyclic nitrogen compound is 2-ethyl-4-methylimidazole.

6. A process as defined in claim 1 wherein the heterocyclic nitrogen compound is 4-methyl imidazole.

7. A process as defined in claim 1, wherein the heterocyclic compound is 2-hydroxypyridine.

8. A process as defined in claim 1 wherein the heterocyclic compound is 4-hydroxypyridine.

* * * * *

UNITED STATES PATENT AND TRADEMARK OFFICE
CERTIFICATE OF CORRECTION

PATENT NO. : 5,442,107
DATED : August 15, 1995
INVENTOR(S) : ROBERT G. BEEVOR and DAVID J. GULLIVER It is certified that error appears in the above-indentified patent and that said Letters Patent is hereby corrected as shown below:

Col. 5, l. 34, formula should read "$R^7=t-C_4H_9$"

Col. 5, l. 64, remove the comma (,) after "to" and before "generate"

Col. 6, lines 31-32, change the column of heading "Final Iodide" to --Iodide--, and change the column heading "Rh" to --Final Rh--

Signed and Sealed this

Sixteenth Day of January, 1996

Attest:

Attesting Officer

BRUCE LEHMAN

Commissioner of Patents and Trademarks